United States Patent
Murphy, Jr. et al.

(10) Patent No.: US 6,604,852 B1
(45) Date of Patent: Aug. 12, 2003

(54) HIGH PRESSURE BRINE CRYSTALLIZATION POINT APPARATUS

(75) Inventors: Robert J. Murphy, Jr., Kingwood, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/733,825

(22) Filed: Dec. 9, 2000

(51) Int. Cl.[7] .............................................. G01N 25/04

(52) U.S. Cl. .......................................... 374/20; 374/24

(58) Field of Search ............................ 374/19, 20, 24, 374/16, 17, 18

(56) References Cited

U.S. PATENT DOCUMENTS

| | | | | |
|---|---|---|---|---|
| 2,951,367 A | * | 9/1960 | Rachford, Jr. ................ | 374/16 |
| 3,077,764 A | * | 2/1963 | Kapff ............................ | 374/19 |
| 3,187,557 A | * | 6/1965 | Holbourne .................... | 374/19 |
| 3,527,082 A | * | 9/1970 | Provot et al. ................. | 374/17 |

(List continued on next page.)

FOREIGN PATENT DOCUMENTS

| | | | | |
|---|---|---|---|---|
| EP | 0 385 035 A2 | | 9/1990 | |
| EP | 0419 677 A1 | | 4/1991 | |
| EP | 1215483 A1 | * | 6/2002 | ........ G01N/25/04 |
| GB | 914 320 A | | 1/1963 | |
| GB | 2043246 A | | 10/1980 | |
| GB | 2 202 941 A | * | 10/1998 | ................ 374/16 |
| JP | 58-162824 | * | 9/1983 | ................ 374/19 |
| JP | 61-132849 | * | 6/1986 | ................ 374/16 |
| JP | 61-217740 | * | 9/1986 | ................ 374/16 |
| JP | 5-45312 | * | 2/1993 | ................ 374/18 |

OTHER PUBLICATIONS

Kaoru Onoe, Sadayasu Inagaki, and Ken Toyokura, "Measurements of Crystallization Temperature in the H2O–LiBr–Salt System," IECEC '97, Proceedings of the 32nd Intersociety Energy Conversion Engineering Conference, Energy Systems, Renewable Energy Resources, Environmental Impact and Policy Impacts on Energy, Honolulu, HI, Jul. 27–Aug. 1, 1997, Intersociety Energy Convers., vol. 3 & 4, Jul. 27, 1997, pp. 2302–2305, XP010268928, ISBN: 0–7803–4515–0.

Aminco Freezing–point depression apparatus (Osmometer), American Instrument Co. Inc., Silver Spreing, MD, Bulletin 2338A, 2 pages, Oct. 1964.*

Siocum, "Multipurpose high–pressure phase–equilibrium apparatus," in Industrial and Engineering Chemistry, Fundamentals, vol. 14, No. 2, (Amer. Chem. Soc.), pp. 126–128, May 1975.*

SPE 58729: Michael A Freeman et al., "High Pressure Crystallization of Deep–Water Completion Brines," 2000 SPE International Symposium on Formation Damage held in Lafayette, Louisiana, Feb. 23–24, 2000. (Society of Petroleum Engineers), 6 pages.

*Primary Examiner*—Diego Gutierrez
*Assistant Examiner*—Stanley J. Pruchnic, Jr.

(57) ABSTRACT

An apparatus and method for determining the crystallization point of high pressure fluids comprising brine are disclosed. The apparatus comprises a temperature probe and an optical fiber probe to determine the temperature of formation and dissolution of crystals during cooling and warming cycles. The apparatus further comprises a pressurization source, preferably a positive displacement pump or connection to a positive displacement pump for pressurizing the sample. The apparatus further preferably includes a jacket for circulating coolant or heat transfer fluid to facilitate cooling of the sample. The method of the invention uses the apparatus of the invention to determine crystallization point of fluid samples.

23 Claims, 1 Drawing Sheet

U.S. PATENT DOCUMENTS

| | | | | |
|---|---|---|---|---|
| 3,956,153 A | * | 5/1976 | Chadha | 252/67 |
| 4,572,676 A | * | 2/1986 | Biermans et al. | 374/20 |
| 4,657,409 A | * | 4/1987 | Wiggin et al. | 374/16 |
| 4,749,856 A | * | 6/1988 | Walker et al. | 374/17 |
| 4,760,538 A | | 7/1988 | Bock et al. | 702/136 |
| 4,770,540 A | * | 9/1988 | Chague et al. | 374/17 |
| 5,082,635 A | * | 1/1992 | Wakatsuki et al. | 422/99 |
| 5,141,329 A | * | 8/1992 | Orlando et al. | 374/16 |
| 5,454,257 A | * | 10/1995 | Per Fotland et al. | 374/16 |
| 5,758,968 A | * | 6/1998 | Diebold | 374/17 |
| 5,933,565 A | * | 8/1999 | Diebold | 374/17 |

* cited by examiner

HIGH PRESSURE BRINE CRYSTALLIZATION POINT APPARATUS

BACKGROUND OF THE INVENTION

1. Field of the Invention

This invention relates to apparatuses for measuring the crystallization temperature of fluids, particularly fluids comprising brine used in oil well completion, workover and drilling operations.

2. Description of Relevant Art

The need to know the crystallization temperature of fluids such as brines and brine-based fluids used in completion, workover and drilling operations in a subterranean formation, particularly a hydrocarbon bearing subterranean formation, is well known. This need is increasingly important for fluids intended for use in the low temperatures and high pressures commonly experienced at the mud line in deepwater wells where any crystallization is undesirable. See Michael A. Freeman et al., High Pressure Crystallization of Deep-Water Completion Brines, SPE 58729 (2000).

Salt crystals, which form and precipitate at or below the crystallization temperature, can lead to problems. Such problems include: plugging of filtration units; and settling in the tank and consequent altering the density of the fluid pumped, possibly to the point the density is insufficient to control formation pressures. Additional crystals forming in brines may also increase the brine viscosity to the point the brine appears as a frozen solid, resulting in line plugging and pump seizure.

Thus, crystallization temperature of a brine or fluid for use in wellbores penetrating subterranean formations is normally part of the specifications for such fluids. The actual crystallization temperature of a brine is said to be that temperature at which a solid will begin to form out of solution if given sufficient time and proper nucleating conditions. The solid may be either salt or freshwater ice. Salt crystals have a smaller specific volume than brine. Thus, brine will not expand in volume during crystallization as seen when drinking water freezes.

The crystallization temperature of a fluid at a given density can be varied by adjusting the composition and concentration of the salts in the fluid.

Three different crystallization temperatures are often quoted for brines. These three crystallization temperatures are:

FCTA (First Crystal To Appear);
TCT (True Crystallization Temperature); and
LCTD (Last Crystal to Dissolve).

The American Petroleum Institute (API) defines FCTA as: "The temperature corresponding to a minimum in a plot of temperature during cooling, or the temperature at which visible crystals start to form." FCTA will generally include some "supercooling effect" or cooling below the actual crystallization temperature. See API Recommended Practice 13J at ¶7.1.12a.

The API defines TCT as: "the maximum temperature reached following the supercooling minimum, or the inflection point in cases with no supercooling," in a plot of temperature during cooling cycle. TCT will equal FCTA if there is no supercooling. See API Recommended Practice 13J at ¶7.1.12b.

The API defines LCTD as: "the temperature at which crystals disappear, or the inflection point on the heating curve," in a heating cycle. See API Recommended Practice 13J at ¶7.1.12c.

The API has warned that the accuracy of a crystallization temperature testing method depends on several factors, most importantly the "supercooling control." According to the API, supercooling or the supercooling effect occurs when a brine is cooled below its actual crystallization temperature. Supercooling may be minimized by slow cooling rates and nucleation of crystallization with selected solid surfaces. Solid surfaces considered effective nucleators for brines include, for example, barium oxide, barium hydroxide, calcium carbonate, and bentonite. Only a very small amount of nucleators is said to be needed to reduce supercooling. See API Recommended Practice 13J at 7.1.14–7.1.15.

According to the API, the best measure of the crystallization temperature of a brine is the TCT. This measured crystallization temperature is said to best represent the temperature at which crystals will precipitate from a brine. FCTA is typically lower than TCT and LCTD is typically higher than TCT. The difference between FCTA and TCT is said to represent the degree of supercooling. If this difference exceeds 5° F. (3° C.), the API recommends repeat of the measurements for crystallization point at a slower cooling rate. See API Recommended Practice 13J at 7.1.20.

In the oil and gas industry, the most common method of determining crystallization temperature of brine calls for cooling a sample of the brine and observing the decreasing temperature until crystals begin to form. The minimum temperature reached before crystallization is recorded as the FCTA temperature. The maximum temperature obtained immediately after crystallization is recorded as the TCT. The sample is then allowed to warm by discontinuing cooling and is observed until all crystals formed during the cooling cycle have dissolved. The temperature at which all of the crystals have dissolved is recorded as the LCTD temperature. See API Recommended Practice 13J 7.3.

This common procedure does not provide for measurement under high pressure. Measurements under pressure, particularly high pressure, are desired because the increased pressure better simulates the conditions found in a subterranean formation. However, measuring crystallization temperature under high pressure has been viewed as not feasible or difficult, because of the need to have a person directly view or "eyeball" the sample for reading the measurements.

A need exists for apparatuses and techniques that afford measurement of crystallization point in fluids under high pressure.

SUMMARY OF THE INVENTION

A method and apparatus are disclosed for determining or measuring the crystallization temperature of fluids at high pressure (i.e., pressures exceeding atmospheric pressure and reaching about 5,000 psig to about 10,000 psig or even as high as about 20,000 psig or more, preferably simulating pressures in a wellbore penetrating a subterranean formation.

The apparatus of the invention comprises a test cell and a pressurization vessel for pressurizing the test cell or for holding or enclosing the test cell at pressures greater than atmospheric pressure and preferably at pressures approximating subterranean formation pressures. Preferably the test cell and pressurization vessel are a single vessel but alternatively they could comprise distinct or separable vessels. The apparatus further comprises a thermometer or other measurer of temperature, i.e., a temperature probe, and optical fibers, preferably comprising a fiber optic probe, capable of being inserted in the test cell and in test fluid to be tested in the test cell.

At least one optical fiber is connected to an external light source and at least one optical fiber is connected to an external light detector, through a suitable high pressure seal. These optical fibers afford observation or determination of crystal formation and dissolution in said sample without need for a person to visually watch said sample.

The apparatus further preferably comprises a jacket for receiving and circulating coolant or heat transfer fluid around the test cell to facilitate cooling of the sample for crystallization.

In the method of the invention, a sample of fluid comprising brine is placed in a test cell, preferably in the apparatus of the invention, and put under pressure (greater than atmospheric pressure). Pressurization is preferably obtained with a positive displacement pump which affords information on changes in the volume of the test fluid, as when crystals are formed in the fluid reducing the fluid volume when compared to the same fluid with such crystals dissolved therein. The sample is then cooled until crystals begin to form and the temperature of the sample when such crystals begin to form is recorded. The sample is then allowed to warm and the temperature when all crystals formed during cooling have dissolved is recorded. Additional temperatures during the cooling and heating or warming cycles may be recorded as desired.

The point at which the crystals begin to form or have completely dissolved may be assessed, observed or determined through the optical fibers, transmitting light to the sample and detecting reflection of said light and transmitting same to a light detector. Crystals will reflect light differently than fluid.

Alternatively, or additionally, changes in volume may be detected and determined. Thus for some brines, the point at which the crystals begin to form or have completely dissolved may also be assessed through a change in volume of the fluid. Further, alternatively or additionally, the point at which the crystals begin to form or have completely dissolved may be assessed by temperature pattern, since formation of the crystals will emit heat into the fluid.

DETAILED DESCRIPTION OF PREFERRED EMBODIMENTS

Figure 1:
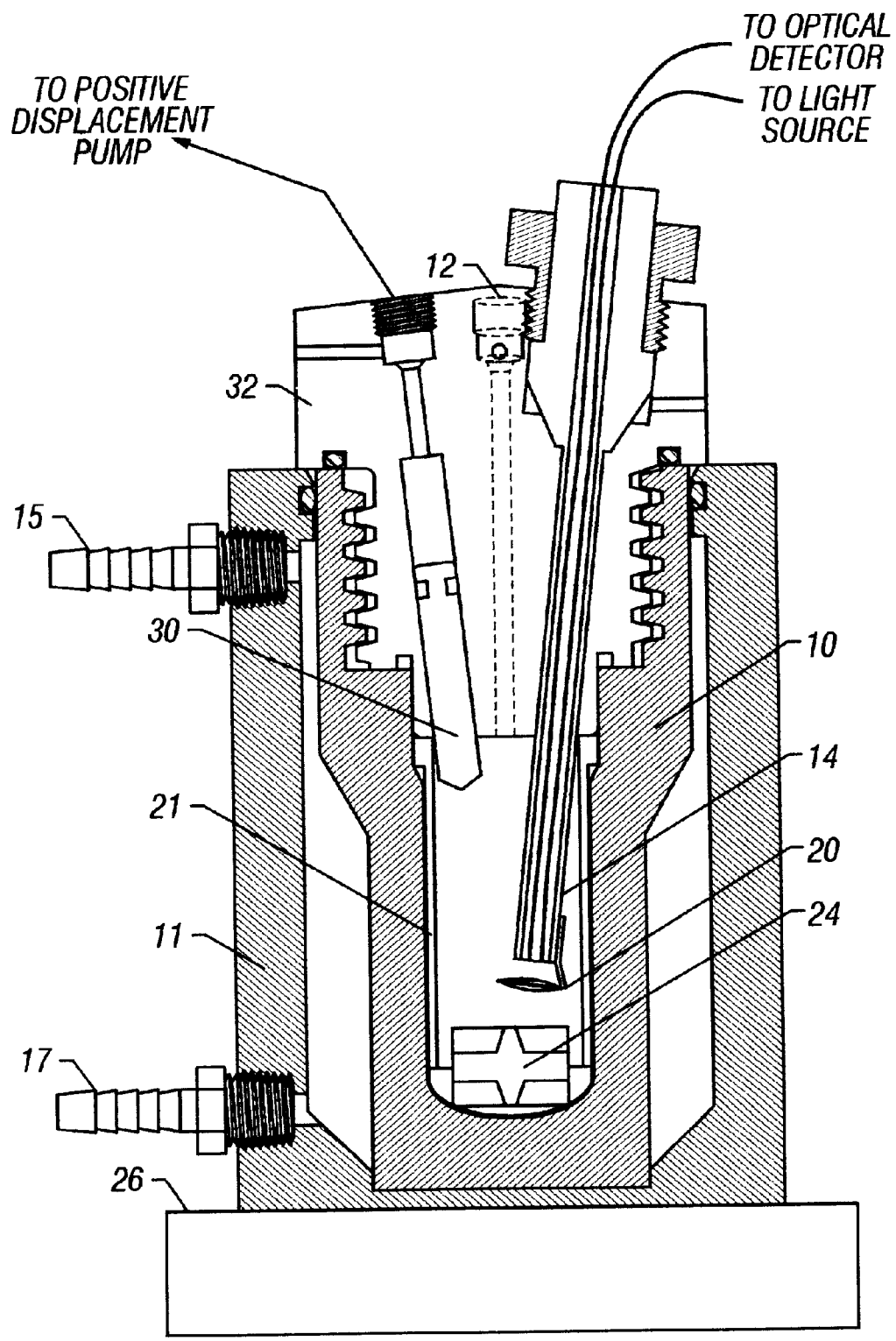
FIG. 1 is a cutaway schematic of a side view of one embodiment of the apparatus of the invention.

Referring to FIG. 1, the apparatus of the present invention comprises a test cell body or test cell 10 sufficiently large to hold a quantity or sample of the fluid for which the crystallization point is to be determined. For example, about 50 ml of fluid are typically used although the invention is not limited to any particular quantity, provided the quantity is sufficiently large to allow for crystallization and detection of same and sufficiently small as to be a reasonable quantity for testing or for fitting into a test cell. The test cell 10 is preferably comprised of a non-magnetic material capable of withstanding test temperatures and pressures, which may be temperatures and pressures commonly found in subterranean formations. One example material suitable for comprising a test cell is metal alloy UNS NO5500, available from Criterion Metals, Inc., Smithfield, R.I., although other non-magnetic materials might alternatively be used, even for example plastic or fiberglass, depending on the test temperatures and pressures desired and the limitations of the material to withstand such planned or desired temperatures and pressures.

The test cell 10 should also be sufficiently large as to accommodate one or more thermometers or other temperature measurers or probes 12 for measuring temperature, such as a thermocouple or RTD temperature probe, inside the test cell 10. Such probe 12 is preferably comprised of stainless steel, and most preferably comprised of 316 stainless steel. Preferably, the apparatus of the invention further comprises a jacket 11 for said test cell, which may be used to surround, envelope or at least partially and preferably completely enclose said cell. Said jacket 11 comprises at least one inlet 15 and at least one outlet 17 for circulating coolant or heat transfer fluid in said jacket 11 to cool the test sample during testing to determine the crystallization point of the fluid. Alternatively, the cell 10 may be cooled in other ways. For example, placing the entire apparatus of the invention in a cold room or refrigerator could be used to cool the fluid test sample in the cell 10 for determining crystallization point of the fluid.

Further, the test cell 10 should be sufficiently large as to accommodate one or more fiberoptic probes or sensors 14 comprising optical fiber or fibers for providing a light source to the cell. The optical fiber provides such light typically by transmitting to the cell light from an external source, or a source external the apparatus of the invention. An example of such a light source is an LED, although any light source capable of having its light transmitted by an optical fiber is suitable for use with the invention. Additionally, the same or a different probe 14 comprises an optical fiber or fibers for collecting reflected light in the cell 10 and transmitting said reflected light to an external optical detector (not shown in FIG. 1). Preferably, a mirror 20 is placed in cell 10 near an end (preferably about ⅜ inch from the end) of the fiber-optic probe 14 in said cell 10 to reflect light back to the probe 14.

Optionally, a liner 21 may be used in the cell 10 to reduce or slow heat transfer to the fluid sample to enable better detection of exothermal heat as the crystals are formed and to control optical properties of the cell interior. Such liner is preferably comprised of plastic.

Optionally, a magnetic stirrer 24 may be used in the cell 10 and the cell may be positioned on a magnetic stirring plate 26 for stirring the fluid sample during testing. Stirring of the fluid sample is essential during testing, but alternative ways of effecting the stirring may be used.

Preferably, the pressurization is effected with a positive displacement pump that allows measurement of the volume of pressurized fluid or pressurization fluid being used. A preferred example pump for effecting such pressurization is a syringe pump made by ISCO, Inc., Lincoln Nebr., which is capable of pressures up to about 10,000 psig. Pressures as high as about 20,000 psig or more may alternatively be used with this invention. Pressurization fluid such as, for example, an oil, acts on an isolation piston 30 that prevents contamination of the fluid sample for which the crystallization point is to be measured. Such piston 30, preferably comprised of plastic or other inert substance, is preferably positioned in cap 32 of the cell 10. Cap 32 is preferably comprised of UNS NO5500. Cell 10 has connections, preferably in or near cap 32, to the pressure source such as a positive displacement pump, and to the temperature probe.

The apparatus of the invention may be used to measure crystallization of fluids consistent with or according to the API Recommended Procedure 13J Section 7. Additionally, the apparatus of the invention has the added ability to make such measurements with the fluid test sample under pressure. In determining crystallization measurements with the present invention, the sample of fluid comprising brine for crystallization point determination is placed inside cell 10. A nucleating agent, such as, for example, barium oxide, barium hydroxide, calcium carbonate, or bentonite, may be added to the fluid sample to reduce or limit supercooling. Probes 12 and 14 are placed in cell cap 32, and cell cap 32 is placed or positioned in the test cell 10 which in turn is positioned in the cooling jacket 11. Coolant or heat transfer fluid is circulated in the cooling jacket 11, the temperature is lowered, and the cooling cycle begins. When crystals begin to form in the fluid sample, the minimum temperature reached before crystallization is recorded as the FCTA temperature. The maximum temperature achieved immediately after crystallization has occurred is recorded as the TCT. Cooling of the sample is then discontinued and the sample is allowed to warm. Dissolution of the crystals formed during the cooling cycle is observed during such warming and the temperature when all of the crystals have dissolved is recorded as the LCTD.

With the apparatus of the present invention, crystallization in the fluid sample may be detected by an optical observation of crystal formation (for example, clear brine becomes translucent or turbid) and by exothermic temperature change. The temperature probe 12 measures the temperature inside cell 10. The change in optical properties of the fluid sample is detected and measured by means of light transmitted into the cell through an optical fiber in fiber optic probe 14 from an external light source to the fluid. An example light source is a yellow LED, but other sources may be used. The light entering the cell is reflected, scattered and absorbed by the crystals in the fluid. Light that is reflected back to the optical fiber probe 14 is collected by an optical fiber and transmitted to an external optical detector. Examples of external optical detectors that may be used for the invention include without limitation cadmium-sulfide photo-resistance detectors and photo transistors.

The apparatus of this invention is not restricted to the use of visible light, although visible light is the type light contemplated for use in the API Recommended Practice 13J.

When a mirror 20 is used in cell 10, crystallization is detected with the apparatus of the invention as a drop in the amount of light that is returned to probe 14 typically or preferably after passing twice through the fluid sample. The last crystal to dissolve LCTD is detected by measuring in a reverse manner; that is, by detecting an increase in the amount of light that is returned to probe 14.

When a mirror 20 is not used, crystallization is detected as an increase in the amount of light due to back scattering of light by the crystals. When the crystals are small, the signal from such back-scattered light may be small.

A particular advantage of the present intention is that volume change of the fluid sample may be detected due to crystallization and temperature changes. The fluid with crystals will have different volume than the fluid without crystals. The ability of the cell 10 to be pressurized enables detection of crystallization point:by combining volume, temperature and optical techniques.

That is, with the present invention, changes in volume may be used to detect crystallization point for some brines (particularly divalent brines) and changes in temperature may be used to detect crystallization point for some brines. Changes in light transmittance may be used to detect crystallization point for most if not all brines. Results with one method of detection may be used to check or verify results with another method of detection.

Another advantage of the present invention is that the crystallization point measurement process may be automated which affords enhanced reproducibility and safer operation. Temperature and pressure controls and measurements, fluid volume measurements, and light level measurements may be done by a personal computer with electronic interface with the apparatus of the invention. The personal computer (PC) may be programmed to determine when to warm and cool as described above to allow multiple cycles of crystallization and redissolving for repetitive and accurate determination of the crystallization points, TCT and LCTD.

The foregoing description of the invention is intended to be a description of preferred embodiments. Various changes in the details of the described apparatus and method can be made without departing from the intended scope of this invention as defined by the appended claims.

We claim:

1. An apparatus for determining crystallization point of a fluid, said apparatus comprising:
   a cell for holding a sample of said fluid;
   a vessel for containing said cell;
   a temperature probe for measuring the temperature of said sample;
   an optical fiber probe comprising optical fibers for transmitting light to said sample from a light source and for receiving or detecting reflected light in said sample and transmitting sample to a light detector, connected to said light source and to said light detector; and
   a pressure source for pressurizing the cell wherein said pressure source comprises a positive displacement pump and pressurization fluid for pressurizing said vessel for pressurizing said cell.

2. The apparatus of claim 1 further comprising a mirror for reflecting light in said sample back to said optical fiber probe.

3. The apparatus of claim 1 further comprising a jacket for cooling or warming said cell.

4. The apparatus of claim 1 wherein said pressurization fluid comprises oil.

5. The apparatus of claim 4 wherein said positive displacement pump is a syringe pump.

6. The apparatus of claim 5 further comprising an isolator to prevent contamination of said fluid sample with said oil.

7. The apparatus of claim 6 wherein said isolator comprises an isolation piston.

8. The apparatus of claim 1 wherein said pressure source allows measurement of the volume of pressurized fluid being used.

9. The apparatus of claim 1 wherein the source of said light transmitted to said sample is a light emitting diode.

10. The apparatus of claim 1 further comprising connection to a computer.

11. The apparatus of claim 1 further comprising a liner for said cell.

12. An apparatus for determining crystallization point of a fluid comprising brine under pressure greater than atmospheric pressure, said apparatus comprising:
   a cell for holding a sample of said fluid whose crystallization point is to be determined;
   a temperature probe for measuring the temperature of said sample while determining the crystallization point of said fluid;
   an optical fiber probe comprising optical fibers for transmitting light to said sample from a light source and for receiving or detecting reflected light in said sample and transmitting same to a light detector, connected to said light source and to said light detector, for optically observing crystallization in said sample for determining the crystallization point of said fluid; and a pressure source for pressurizing the cell above atmospheric pressure while determining the crystallization point of said fluid.

13. The apparatus of claim 12 further comprising a vessel for containing said cell and said pressure source.

14. A method for determining crystallization point of a fluid comprising brine under pressure, said method comprising:

providing a sample of said fluid;

placing said sample in a container capable of being pressurized and cooled;

inserting in said sample a probe for measuring temperature;

inserting in said sample at least one fiber optic probe comprising at least one first optical fiber connected to a light source for transmitting light to said sample, and comprising at least one second optical fiber connected to a light detector for receiving back reflected light from said sample for effecting optical observation of said sample;

pressurizing said container;

cooling said container;

optically observing said sample and detecting formation of crystals in said sample during said cooling;

observing or recording the temperature of said sample when said crystals begin to form;

stopping said cooling after said crystals begin to form;

allowing said sample to warm; and observing or detecting the temperature of said sample when all crystals have dissolved in said sample during said warming.

15. The method of claim 14 further comprising adding a nucleating agent to said sample prior to said cooling.

16. The method of claim 15 where said pressurizing is to a level that simulates the pressure in a subterranean formation.

17. A method for determining crystallization point of a fluid comprising brine under pressure, said method comprising:

providing a sample of the fluid;

providing an apparatus comprising a cell for holding the fluid sample, a temperature probe, an optical fiber probe comprising one or more optical fibers connected to a light source and to a light detector for optically observing said sample, means for pressurizing said sample in said cell, and means for cooling said sample in said cell;

placing said sample in said cell such that said temperature probe and optical fiber probe, are at least partially in said sample;

pressurizing said sample;

cooling said sample and monitoring the temperature of said sample and optically observing the light transmittance of said sample during said cooling;

allowing crystallization to occur in said sample; and discontinuing cooling said sample after crystallization occurs, allowing said sample to warm after the crystallization, and monitoring the temperature of said sample and optically observing the light transmittance of said sample during said warming until all crystals have dissolved in the sample.

18. The method of claim 17 wherein said monitorings of the temperature together comprise recording at least one of the temperatures in the group comprising the FCTA, the TCT and the LCTD.

19. The method of claim 17 wherein said apparatus further comprises a mirror for reflecting light in said sample in said cell back to said probe.

20. The method of claim 17 wherein said apparatus further comprises a liner in said cell for slowing heat transfer to said sample in said cell.

21. The method of claim 20 wherein said liner controls optical properties of the interior of said cell.

22. The method of claim 17 wherein said pressurizing simulates pressures in a wellbore penetrating a subterranean formation.

23. The method of claim 17 wherein said pressurizing ranges between about 5,000 psig and about 20,000 psig.

* * * * *